(12) United States Patent
Sykes

(10) Patent No.: US 7,905,152 B2
(45) Date of Patent: Mar. 15, 2011

(54) SHEAR TEST APPARATUS AND METHOD

(75) Inventor: Robert John Sykes, Essex (GB)

(73) Assignee: Nordson Corporation, Westlake, OH (US)

(*) Notice: Subject to any disclaimer, the term of this patent is extended or adjusted under 35 U.S.C. 154(b) by 292 days.

(21) Appl. No.: 12/161,055

(22) PCT Filed: Feb. 16, 2007

(86) PCT No.: PCT/GB2007/000528
§ 371 (c)(1),
(2), (4) Date: Jul. 16, 2008

(87) PCT Pub. No.: WO2007/093799
PCT Pub. Date: Aug. 23, 2007

(65) Prior Publication Data
US 2010/0116063 A1    May 13, 2010

(30) Foreign Application Priority Data

Feb. 17, 2006 (GB) ................................. 0603243.7
Oct. 27, 2006 (GB) ................................. 0621462.1

(51) Int. Cl.
G01N 3/24 (2006.01)
(52) U.S. Cl. ............................................. 73/842; 73/760
(58) Field of Classification Search ............. 73/760–842
See application file for complete search history.

(56) References Cited

U.S. PATENT DOCUMENTS

| | | | |
|---|---|---|---|
| 3,603,152 A | 9/1971 | Alibert et al. | |
| 3,662,312 A | 5/1972 | Thorp et al. | |
| 3,756,289 A | 9/1973 | Rotert et al. | |
| 3,805,601 A | 4/1974 | Jeffers | |
| 3,821,785 A | 6/1974 | Rose | |
| 4,280,350 A | 7/1981 | King et al. | |
| 4,869,043 A | 9/1989 | Hatzinikolas et al. | |
| 5,166,910 A * | 11/1992 | Batzle et al. | 367/191 |
| 5,178,005 A * | 1/1993 | Peterson | 73/152.11 |
| 5,255,562 A * | 10/1993 | Yamamoto et al. | 73/160 |

(Continued)

FOREIGN PATENT DOCUMENTS

EP    0772036 A2    5/1997

(Continued)

OTHER PUBLICATIONS

U.S. Patent and Trademark Office, Office Action in U.S. Appl. No. 11/573,005, Oct. 13, 2009.
U.S. Patent and Trademark Office, Office Action in U.S. Appl. No. 11/573,005, Apr. 2, 2009.
European Patent Office, International Search Report and Written Opinion in Serial No. PCT/GB2007/000528, May 9, 2007.

*Primary Examiner* — Max Noori
(74) *Attorney, Agent, or Firm* — Wood, Herron & Evans, L.L.P.

(57) ABSTRACT

A test apparatus for applying shear loads to a deposit on a substrate comprises a cantilevered shear tool (18) having a tip (24) for contact with the deposit, and a back face having a piezo-electric crystal thereon. In use, the back face is subject to a compressive force, as well as other forces, and a corresponding electrical output from said crystal which is proportional to those forces. In one embodiment, the portion of the shear tool which contacts the deposit is offset rearwardly from the front face of the shear tool to improve the accuracy of the signal produced by the piezo-electric crystal. The apparatus is useful in testing the strength of bonds between deposits and substrates typically found in semiconductor devices.

31 Claims, 6 Drawing Sheets

U.S. PATENT DOCUMENTS

| | | | |
|---|---|---|---|
| 5,564,170 A | 10/1996 | Flemmer et al. | |
| 5,938,503 A * | 8/1999 | Cook et al. | 451/10 |
| 5,958,270 A | 9/1999 | Cho | |
| 6,041,996 A | 3/2000 | Arikado | |
| 6,131,795 A | 10/2000 | Sato | |
| 6,341,530 B1 | 1/2002 | Sykes | |
| 6,901,795 B2 | 6/2005 | Naguib et al. | |
| 7,413,108 B2 | 8/2008 | Vasquez et al. | |
| 7,500,378 B2 | 3/2009 | Tsai et al. | |
| 7,555,961 B2 | 7/2009 | Sykes | |
| 2006/0011703 A1 | 1/2006 | Arita et al. | |
| 2008/0314159 A1 | 12/2008 | Sykes | |

FOREIGN PATENT DOCUMENTS

| | | |
|---|---|---|
| GB | 1094862 | 12/1967 |
| GB | 2174241 A | 10/1986 |
| JP | 1174935 A | 7/1989 |
| SU | 1727039 A1 | 4/1992 |
| WO | 00/75624 A1 | 12/2000 |
| WO | 2004/083831 A1 | 9/2004 |
| WO | 2005/114722 A1 | 12/2005 |
| WO | 2006/016136 A2 | 2/2006 |

* cited by examiner

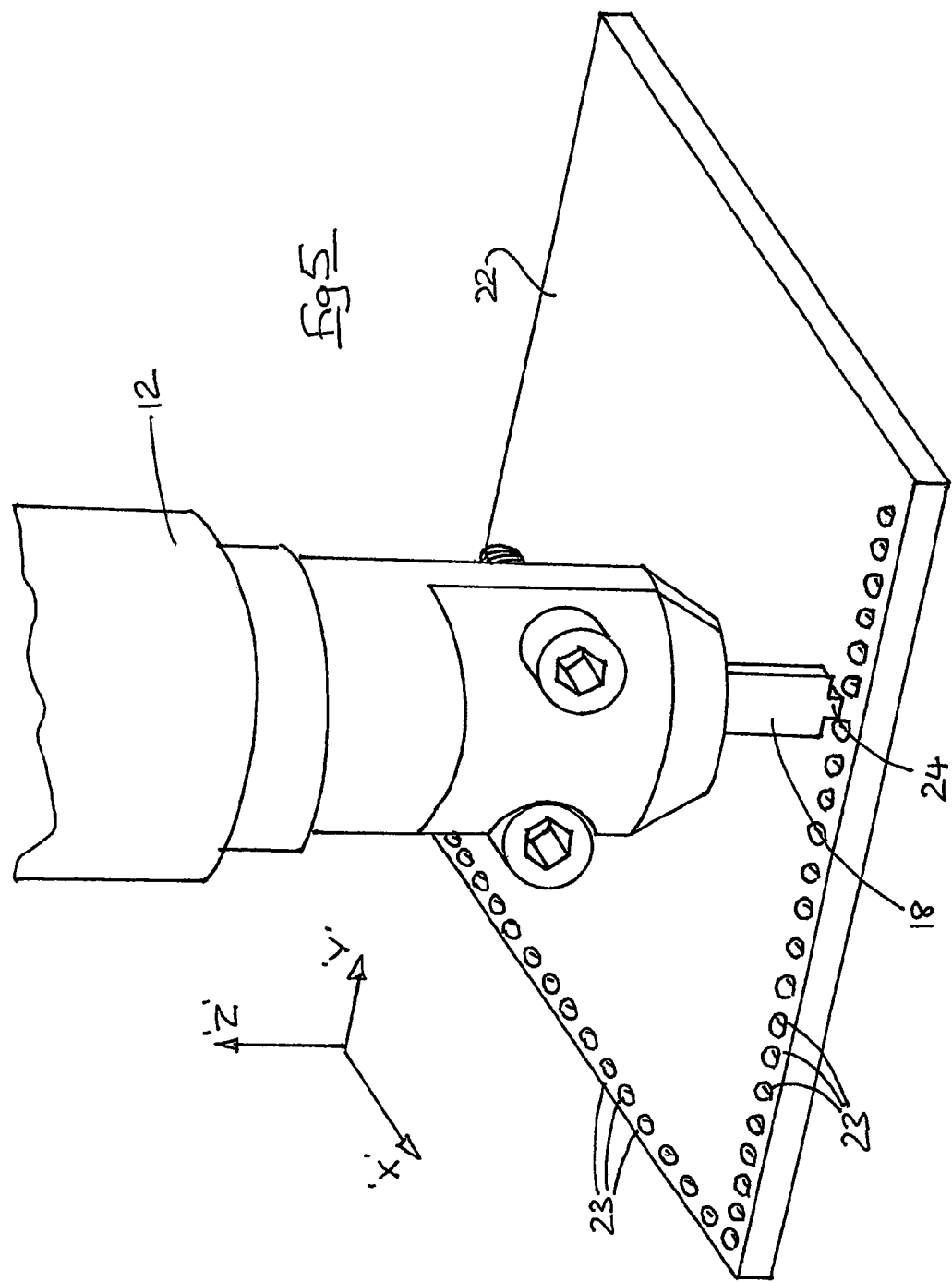

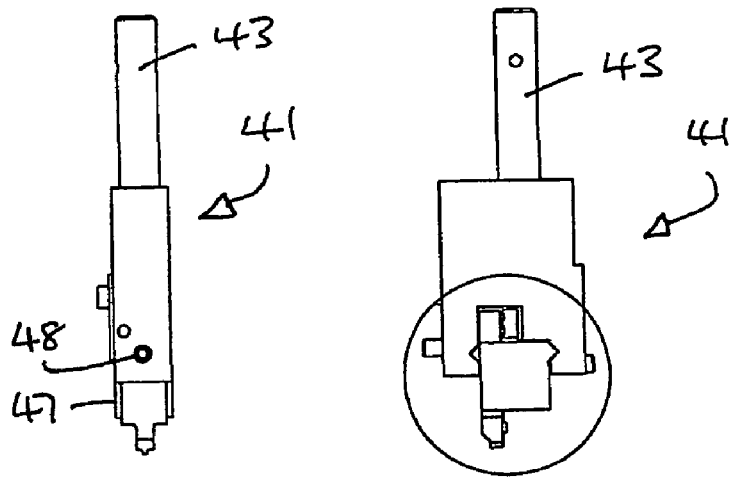
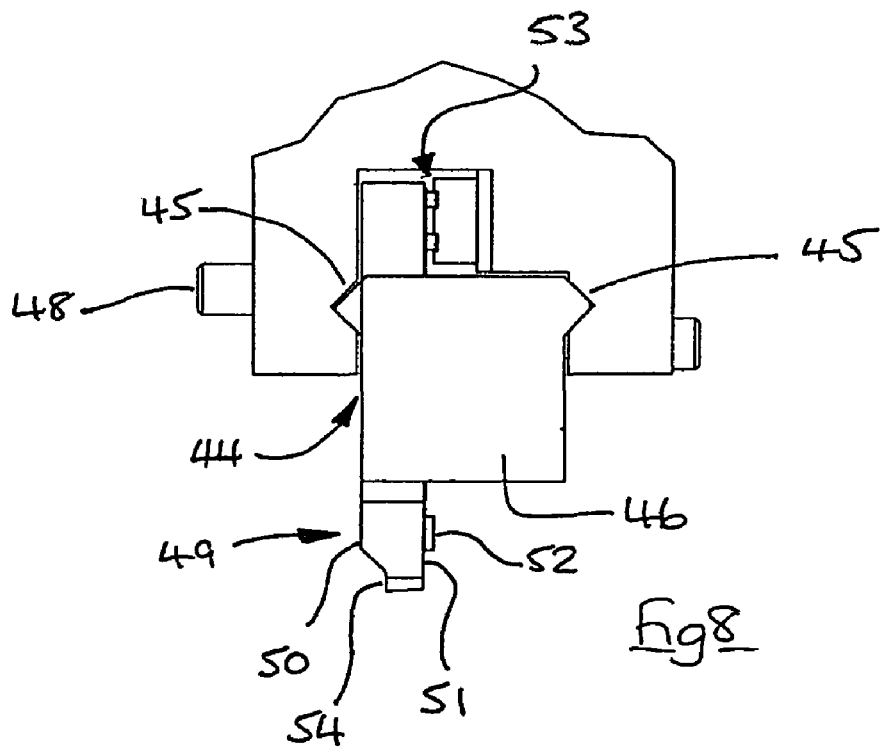

SHEAR TEST APPARATUS AND METHOD

This invention concerns apparatus and methods for testing the shear strength of a bond in a semi-conductor device, and more particularly the strength of a bond between a substrate and a means of electrical connection thereto, typically a part-spherical deposit. Such deposits can be of solder, gold or other materials and are sometimes referred to as solder bumps or ball grid arrays.

Semiconductor devices are very small, typically from 0.2 mm square to 25 mm square. These devices have sites for the bonding of electrical conductors thereto. Sites typically comprise part spherical electrically conductive deposits of for example gold or solder, collectively known as balls, which in use have the appearance of a squashed sphere or low circular dome, and a diameter in the range 50-1000 µm. These deposits form part of the electrical path between, for example, a printed circuit board and a chip, and may directly connect components, or may be joined to a conductor which is itself connected to another component. Many such balls may be provided as a regular grid-like array on a substrate.

Discrete balls are typically applied to a substrate and reflowed during subsequent connection to another component.

It is necessary to test the mechanical strength of the bond between the gold or solder deposit and the substrate in order to give confidence that the bonding method is adequate, and that the bond strength is sufficient. Difficulties arise because of the very small dimensions of the components, the precision with which the testing device must be positioned, and the very small forces and deflections which are to be measured.

It has been proposed to test the shear strength of such deposits by applying a tool to one side thereof. In order to avoid friction caused by the tool rubbing on the surface of the substrate, it is necessary for the tool to be just above the substrate surface. The height of the tool above the substrate must be closely controlled, typically within ±0.001 mm, to give accurate force measurement.

A known shear test apparatus comprises a machine having a support surface and a test head movable in a controlled manner relative to the support surface. The test head carries a cartridge specific to the test to be performed and having one of several interchangeable tools thereon. Typically the tool will be sized and/or shaped to suit the ball deposit to be tested. In use, the substrate to be tested is attached to the support surface, and the tool is mounted into the cartridge and driven against the ball deposit to perform the required test, which may be for example a shear test or a reciprocating fatigue test. Typically the tool moves against a stationary deposit.

It will be understood that a typical tool is very small, and accordingly the cartridge has a flexible element on which is mounted one or more force gauges (such as strain gauges). Thus shear force between the tool and ball deposit is measured at a distance by deflection in the flexible elements of the cartridge. WO-A-2005/114722 shows an example of such a cartridge.

In the case of impact testing, where the tool is moving at high velocity before contact with the ball deposit, shear forces are not easy to detect. This is because the strain gauged element is somewhat remote from the tool, and the inertia of the support element masks the forces being measured. Typically the speed of the test is sufficiently high that the test is over before the strain gauge has time to respond to the forces at the tool.

What is required is a solution to this disadvantage of the prior art, in particular a test apparatus and test method better able to detect shear forces at a ball deposit when the shear tool is moving at high speed. Such shear forces may be as a result of a uni-directional or a reciprocating load.

According to a first aspect of the invention there is provided a test apparatus for applying shear loads to a ball deposit of electrically conductive material on a substrate, the apparatus comprising a support element, and a piezo-electric crystal on the support element, the support element being adapted to apply a shear load to a ball deposit, and said crystal being arranged to be placed under stress, thus causing an electrical signal to emanate therefrom. The electrical signal is processed to provide a measure of the shear force experienced by the support element, which in the preferred embodiment is a shear tool.

In such apparatus, the piezo-electric crystal can be arranged close to the contact face of the support element and in any location subject to a strain sufficient to give a detectable electrical signal. Preferably the support element is provided as a cantilevered beam, with the piezo-electric crystal supported on the cantilevered beam.

Electrical connection to the crystal may be by means of conventional wiring, for example a pair of flexible electrical conductors of suitable cross-sectional area. Alternatively the electrical pathways may be provided via the material of the support element on which the piezo-electric crystal is mounted. Insulation to separate the electrical feed and return may be provided in any conventional manner, for example by external insulation of flexible wires, or by a dielectric material separating components of a support element, or by a combination of these. In one embodiment the support element provides electrical feed and return pathways whereas in another embodiment insulated flexible wires provide the feed and return electrical pathways.

The piezo-electric crystal is in one preferred embodiment applied to the back face of the shear tool, or support element, the front face being adapted to apply said shear load. An advantage of providing the piezo element on the back side of the support element is if the piezo element were provided on the front face of the support element, when the front face shears the ball deposit of the substrate, the ball deposit could impact against the piezo element.

In such an arrangement, the front face which is adapted to contact the ball deposit, is necessarily placed in tension as its shears the ball deposit of the substrate. The opposite, back, face provides a convenient mounting for a piezo-electric crystal. While the front face it is placed in tension as the ball deposit a sheared, at the same time, the back face is necessarily placed in compression and the piezo element mounted on to the back face is stressed by the compressive forces acting along the back face. Preferably the mounting face of the crystal is planar and closely adjacent the portion of the support element which is adapted to contact the ball deposit, in use.

The piezo-electric crystal can, be of any suitable shape or thickness. Generally speaking one face thereof is preferably planar, most preferably flat, to permit mounting to the support element. A crystal may be calibrated to determine the relationship between stress and electrical output, and the shape thereof may be selected to give a desirable characteristic. In the preferred embodiment the crystal is a rectangular planar member having substantially equal transverse dimensions and in edge alignment with the Z axis and it is mounted on the back side of the support element which is subjected to compressive strain when shearing a ball deposit as discussed above.

Although this specification refers to the use of a single piezo-electric crystal, it is envisaged that more than one crystal may be provided to detect forces in directions other than corresponding to the direction of the application of force. For example off-centre loads may give a lateral strain which is useful in determining the nature of the bond to be tested. Thus the invention envisages one or more piezo-electric crystals mounted on a support element and arranged to be placed under stress in different directions with respect to the direction of application of force. The apparatus of the invention may include electronic resolution of inputs from several piezo-electric crystals so as to obtain information about the direction of failure force on a ball deposit.

In use the support element is retained by a tool holder which in turn is mounted in a known shear test machine having capability of movement in the X, Y and Z axes.

Such an arrangement provides a convenient means of adapting a shear test machine to different shear tests, in particular by allowing the shape of the support element to be selected according to the nature and shape of the ball deposit, and the likely shear forces to be applied. Thus ball deposits of larger size and likely having better adherence can be tested with a support element of appropriate size. More particularly the output range of the piezo-electric crystal can be optimised to give high sensitivity in the range of shear force anticipated. Furthermore the shape of the support element in the region of contact with the ball deposit can be selected to suit the intended test, for example from a range comprising a flat planar contact face, a one dimensional curved contact face adapted to the approximate diameter of the ball deposit, and a two-dimensional curved contact face adapted to the approximate sphericity of the ball deposit. It will be understood that ball deposits are typically somewhat irregular in shape, so that an approximation of the size and shape of contact face is required.

The support element may for example be a substantially rectangular block having parallel front and rear faces, the front face having the contact face for the ball deposit, and the back face having the piezo-electric crystal mounted thereon.

In one embodiment the support element is a spade-like tool having a flat back face to which said crystal is mounted. The front face of the support element may be adapted to the shape of the ball deposit to be tested, for example by having a part spherical recess adapted to engage a portion of the circumference of the ball deposit.

The contact face of the support element may be reduced in size to correspond closely to the diameter of the ball deposit to be tested. In particular the support element may comprise a main body portion to which the piezo-electric crystal is mounted, and a protruding contact portion of reduced size.

This arrangement has a number of advantages. In particular, the main body portion can be sized to accommodate a piezo-electric crystal of desired proportions regardless of the size of the contact portion. The contact portion may be made small enough to engage individual but closely adjacent ball deposits, without requiring a correspondingly small support element and piezo-electric crystal. The base of the contact portion may also be made small enough to land upon a flat portion of a substrate between closely adjacent ball deposits, so as to ensure a precise lifting distance off of the substrate prior to a shear test; as noted in the introduction such lift is necessary to avoid rubbing friction. Finally, variation of the proportions of the support element relative to the proportions of the contact portion permits the range of stress in the region of the piezo-electric crystal to be selected; thus a preferred size and shape of piezo-electric crystal may be adapted to a range of differently sized and shaped contact portions.

The piezo-electric crystal may be mounted to the support element in any suitable manner which allows stress to be transmitted thereto in a consistent and repeatable manner. One suitable method of mounting is surface bonding by an adhesive such as epoxy resin.

In a preferred embodiment the interface between the support element and the crystal comprises a force distributing layer which is adapted to give substantially uniform planar contact. Such a layer may for example comprise an epoxy resin which is spread whilst fluid onto the respective interface surfaces, and cures after assembly of the apparatus to ensure that planar contact occurs.

The layer need only be very thin, and sufficient only to accommodate any misalignment which may be present in the respective surfaces. A particular advantage of epoxy resin is that the adjacent components are also retained in one another adhesively, so that the apparatus becomes unitary.

Thus the adhesive layer comprises a thin cushion between the support element and the piezo-electric crystal, and has the second function of mechanically retaining the support element and piezo-electric crystal in permanent robust engagement.

The layer of epoxy resin may also provide an electrical insulator for the crystal or, depending on the electrical pathways, may be electrically conductive. Such an arrangement is particularly advantageous in cases where one or more flexible wires is considered undesirable.

In a preferred embodiment the support element is provided with an inset contact portion for contact with the ball deposit. The contact face is typically set back by 30-60% of the overall width of the support element. The plane of the inset is preferably orthogonal to the intended direction of application of shear force, and is typically substantially orthogonal to the substrate and in the Z axis. In one embodiment the plane of the inset is parallel to and between planes defining the front and back faces of the support element.

The exact location of the inset face is preferably determined so that vertical loads on the underside of the tool pass through a neutral plane with respect to the mounting face of the piezo-electric crystal, so that the output thereof is not affected. This adaptation and/or interpretation of the electrical output of the piezo-electric crystal is not required; in particular the electrical output is preferably proportional to the strain exerted thereon, and to the applied shear force. Most preferably the relationship between applied shear force and electrical output is linear. The location of the inset is determined by the required shape and dimensions of the support element, but can be predicted by the use of mathematical methods such as finite element analysis (FEA) and checked by empirical application of vertical (Z direction) loads.

In a preferred embodiment the inset is orthogonal to the intended direction of shear, and is connected to the front face of the support element by an angled or radiused face so as to eliminate points or lines of high stress.

Other features of the invention will be apparent from the following description of several preferred embodiments shown by way of example only in the accompanying drawings in which:

FIG. 5 is a representation of the tool holder of FIGS. 1-4 in use.

FIG. 6 shows a variant in front elevation.

FIG. 7 shows the variant of FIG. 5 in side elevation.

FIG. 8 is an enlarged view of part of FIG. 7;

Figure 13:
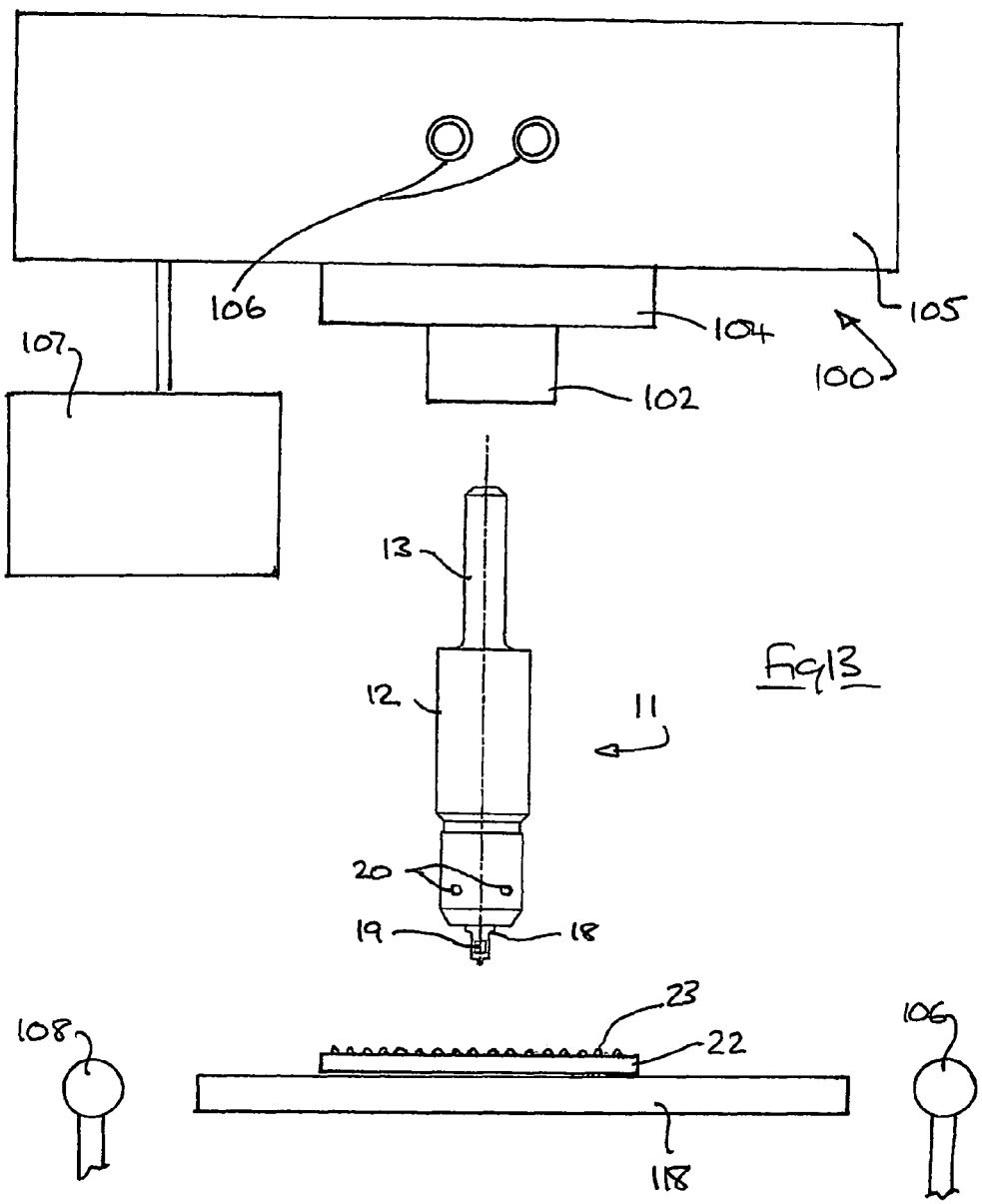

FIG. 13 schematically depicts a bond testing machine in which the improved shear testing tool of the present invention could be used.

Figure 1:
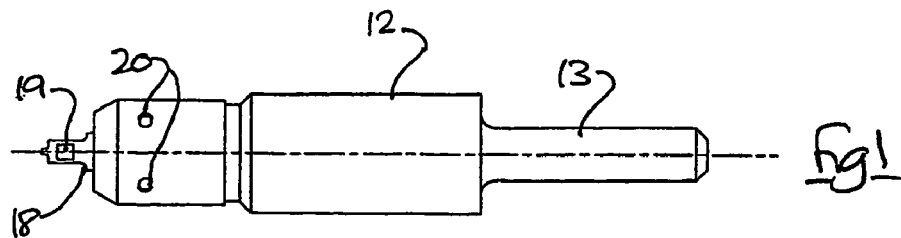
FIG. 1 is a side elevation of a tool holder incorporating the invention.
Figure 2:
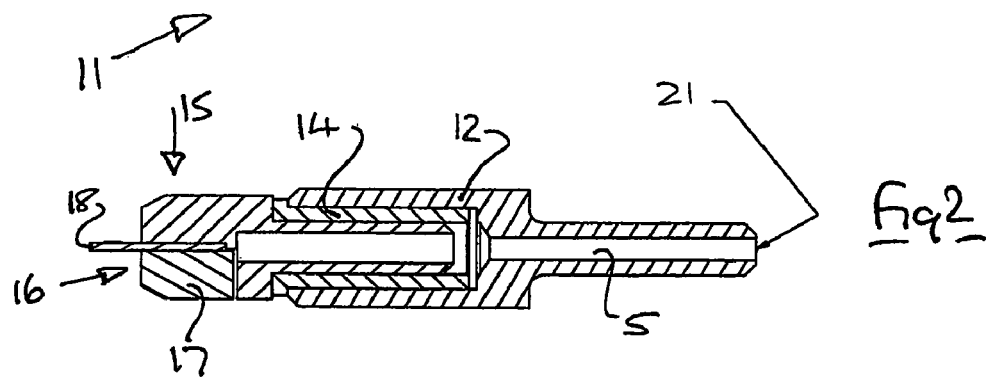
FIG. 2 is an axial cross-section through the holder of FIG. 1, turned through 90°.
Figure 3:
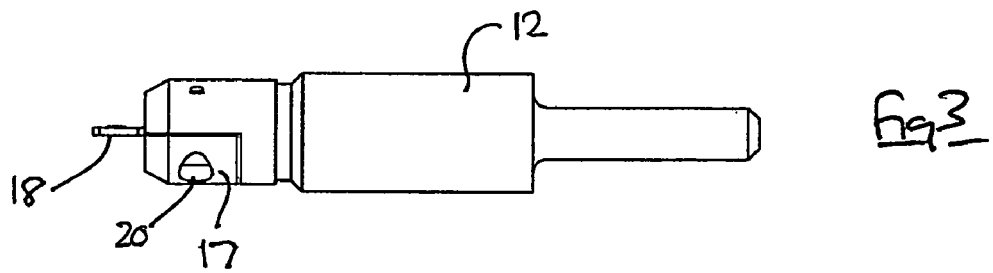
FIG. 3 is a side elevation corresponding to FIG. 2.

With reference to FIGS. 1-4, a tool holder 11 comprises a tubular body 12 having a reduced diameter shank 13 for attachment to a test machine such as the bond test machine 100 schematically illustrated in FIG. 1A. The shank 13 is secured in the machine by means of a collet chuck or the like such as chuck 102 of FIG. 1A. The tubular body 12 is for example of metal, preferably a suitably stiff material such as steel. Pressed into the mouth of the tubular body 12 is an annular insulator 14 of any suitable dielectric material, such as a non-conductive plastic. Pressed into the insulator 14 is a tool holder 15 of e.g. steel, and having a split clamp 16 at the proximal end comprising a removable cap 17 secured by socket head screws 20, as illustrated.

The split clamp 16 allows insertion and removal of a support element, or shear tool, 18 on which is mounted a piezo-electric crystal 19. The shear tool is of ceramic material, and comprises a flat plate of substantially constant thickness. The tool 18 is housed in a corresponding recess of the tool holder so that it is retained and gripped when the screws 20 are tightened. The shear tool 18 is mounted as a cantilevered beam, with the piezo-electric crystal 19, in the preferred embodiment, mounted along the central area of the length of the beam.

This invention relates to a device for testing the shear strength of a bond in a semiconductor device and more specifically to a shear tool assembly comprising shear tool 18 and crystal 19. Removable mounting of the tool holder 11 in a test machine is desirable, but not essential, and in the case of removable mounting, the means of mounting is not important save that a suitably rigid and secure connection is ensured.

Likewise, a removable shear tool 18 is not essential, but may be advantageous to permit different shear tools to be fitted to a common tool holder 16. It will be understood that a shear tool 18 may be fixed in a test machine so as to be semi-permanent; in other words removable thereof is envisaged only in case of breakage or other kind of malfunction. Such an arrangement would be beneficial in the event of repeated testing of the same component, where a removable tool holder and/or shear tool may be beneficial in the case of frequent changes in test procedure and/or product.

It is envisaged that the tool holder and shear tool could be permanently connected, for example by epoxy adhesive, in which case a removable cap 17 is not required.

Bond testing machines capable of doing ball deposit shear tests are available in the art. One example is the Model 4000 Series machine available from Dage Precision Industries, Ltd. of Aylesbury, United Kingdom. FIG. 13 schematically illustrates a bond test machine having many elements in common with Model 4000 machine. In the FIG. 13 machine, the shank 13 of the tool holder 11 which holds shear tool 18 is secured in a chuck 102 which is in turn mounted on a tool mover 104. Tool mover 104 provides movement in the X direction, for example, of the shear tool 18 to shear a ball deposits 23 off substrate 22 and movement in the Z direction to vertically position the shear tool 18 with respect to the ball deposits 23. Substrate 22 is mounted on table 118 which provides for movement of the substrate in the X and Y directions relative to shear tool 18. Tool mover 104 is secured to a housing 105 upon which is mounted a high-powered microscope 106. Housing 105 can also include the processor which processes the electrical signals received from the piezo-electric crystal 19 and preferably displays the results of that processing on a display screen 107 which is attached to the housing 105. The machine 100 also includes joystick controls 106, 108 which move the X-Y table 118 and shear tool 18. The operator looks through the high-powered microscope 106 at the area of the substrate 22 of interest and uses the joy sticks 106, 108 to position the shear tool 18 adjacent to the ball deposit 23 to be sheared off of the substrate 22. Once the shear tool 18 is properly position with respect the ball deposit 23, the tool mover 104 moves the tool 18 a desired distance in the X direction, at a desired speed, to shear the ball deposit 23 off of the substrate 22. During this shear event, the piezo-electric crystal 19 experiences forces of tension and compression in a manner later described in more detail. The forces which act upon the piezo-electric crystal 19 produce an electric signal from the crystal 19 which can be correlated to the shear force required to shear the ball deposit 23 off of the substrate.

The electric signal produced by the piezo-electric crystal can be conveyed by insulated wires (not shown) passing through the aperture 5 within the body 12 to exit at the distal end 21 and then up into the processor (not shown) contained within housing 105. In one embodiment, suitable electric tracks may be formed by photo-resist printing on the surface of a ceramic shear tool 18, and provided with push-on electrical connections at the surfaces at which the tool is secured to the tool holder 15. In this embodiment the ceramic shear tool 18 provides the dielectric material onto which the conductive tracks are provided. Conductive tracks may be provided in other ways, for example by bonding or otherwise fixing metallic elements to the ceramic tool 18.

Figure 4:
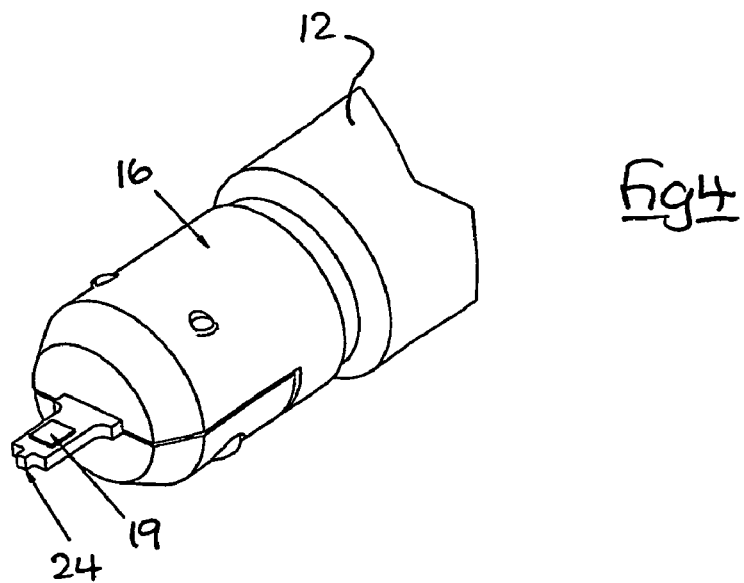
FIG. 4 is a perspective view of the head of the tool holder of FIG. 1, on an enlarged scale.

The tip 24 of the shear tool 18 is reduced in width, as illustrated best in FIG. 4 to correspond closely to the actual width of the connection balls to be tested. The shear tool 18 typically has a width/thickness proportion in the range 3:1 to 8:1, and the tip 24 is typically 1000 µm or less. As illustrated the ratio of the width of the tip 24 to the width of the shear tool 18 may be in the range 4:1 to 10:1.

FIG. 5 shows a test tool in use. The body 12 of the tool holder is mounted on a suitable test machine such as the one shown in FIG. 1A having X, Y, Z traverse as depicted and as previously described is moved relative to a substrate 22 so as to be in position to apply a shear force to one of a number of ball deposits 23. Suitable contact sensing apparatus may be provided to ensure that drag of the shear tool 18 on the substrate 22 is avoided while the shear tool 18 is shearing the ball deposit 23 off the substrate 22.

Two edge rows of balls 23 are illustrated, but any shape of array may be encountered, including a grid array covering the face of substrate 23.

The test is performed by moving the shear tool 18 against the respective ball 23 in the 'X' direction, and applying a progressively increasing force until breakage occurs. The test may alternatively be performed by moving the shear tool 18 at speed, for example at a speed in the range 0.5 to 2.5 msec relative to the ball deposit 23 to dynamically shear the ball deposit 23 off of substrate 22. The speed of tool movement may be up to 10 m/sec dependent on the capabilities of the apparatus, but generally speaking the lowest speed commensurate with effective testing is suitable.

The shear tool 18 is cantilevered out from the body 12 so that in use loads on the front face of the shear tool 18 experienced while the tool 18 is shearing a ball deposit 23 of the substrate 22 place that face in tension. At the same time, the rear face is placed correspondingly in compression. Accordingly the piezo-electric crystal 19 is stressed by the compressive forces acting on the rear face and the crystal 19 generates an electrical output which can be used to determine the force required to shear the ball 23 of the substrate 22.

Tests may be repeated for some or all of the ball deposits of a substrate, and in the case of a regular array the test may be automated.

This embodiment describes use of a single piezo-electric crystal having an aperture compressive axis generally in the Z direction, orthogonal to the plane of movement during shear testing. If necessary or convenient, several crystals may be utilized to detect strain in several mutually different directions, and the several electrical outputs be used severally or in combination to resolve shear force in a desired direction of interest.

If required the tool 18 may be calibrated by repeated shearing of a material of known size and quality, for example a wire end indexed upwardly through a close fitting hole in a substrate. According to this method, a fixture holding the test wire would be secured on the table 118. The shear tool 18 would then be positioned adjacent to the wire end in the same way in which it is positioned relative to a ball deposit. The machine would then be activated to shear off the end of the test wire. Given that the test wire is of a known material and geometry, the forces required to shear the test wire are known. Thus, the electric signal produced by the piezo-electric crystal 19 can be correlated to a known sheer force values. In this way a table of the piezo-electric crystal 19 signal outputs for given shear force values can be generated for the particular shear tool 18 being tested. These values can then be used in the machine processor to indicate shear forces required to shear off ball deposits based on the electrical signals received from the piezo-electric crystal 19.

A variant of the invention is illustrated in FIGS. 6-8. In this variant a tool holder 41 has a mounting shank 43 and a mouth 44 having opposed 'V' grooves 45 to receive a shear tool insert 46. The insert slides 46 into the holder 41 along the axis of the grooves 45 and into abutment with a stop plate 47. The insert 46 is arranged to be retained by a spring loaded ball catch (not shown), and secured by a grub screw 48 so that it becomes immovable with respect to the tool holder 41.

Depending from the insert 46 is a ceramic shear tool 49 having a front face 50 for contact with a ball deposit, and a back face 51 having a piezo-electric crystal 52 mounted thereon. In use, as previously described, shear loads applied at the front face to ball deposits 23 cause a compressive stress to be applied to the crystal 52 with a resulting electrical output. The tool 49 has similar overall proportions to the tool illustrated in the first embodiment.

Suitable sliding electrical connections 53 are provided between the piezo-electric element 52 of insert 46 and the tool holder 41, so as to engage automatically by brushing as the tool holder 41 is inserted.

The contact face 54 of the shear tool 49 is set back from the front face as illustrated. In use, as the shear tool breaks through a ball deposit, in addition to the horizontal forces generated, vertical forces are also generated. The vertical forces, if significant, affect the output of the crystal 52 and may be sufficient to distort the measured forces. Ideally, only the horizontal force necessary to shear the ball deposit off for the substrate should be registered by the crystal 19.

By setting the contact face 54 closer to the mounting face of the crystal, the vertical forces can be directed into a neutral plane so that measurement of bending stress and strain at the mounting face is relatively undistorted. FIGS. 8A, 8B and 8C illustrate this feature of the invention.

Figure 9:
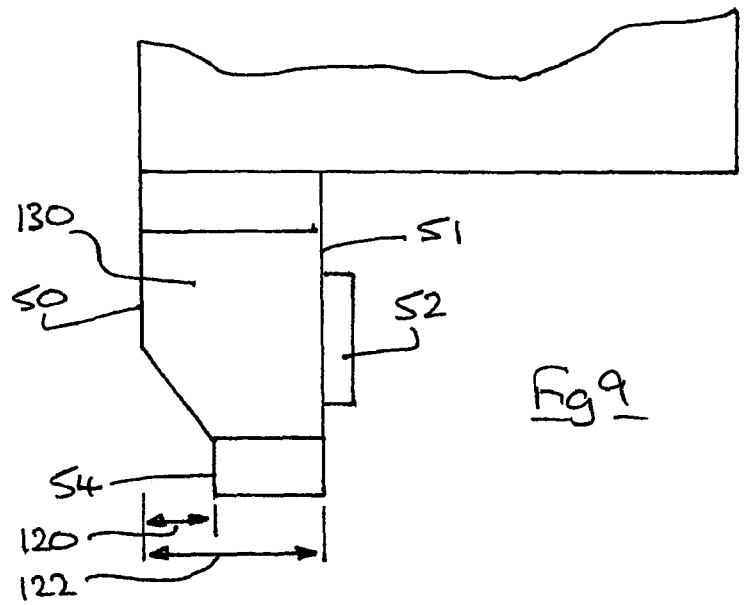
FIG. 9 is a further enlarged view of a part of FIG. 8.

As illustrated in FIG. 9, the contact face 54 is set back a distance 120 which, in this embodiment, is approximately 40% of the distance 122 from the front face 50 to the back (mounting) face 51. The actual set back 120 selected for a particular shear tool 49 is dependent on the overall dimensions of the shear tool 49 and the size and position of the piezo crystal 52.

The set back 120 may also be influenced by the shape of the ball deposit, and the form of the contact face 52. In use the size of set back 120 is typically in the range 30-60% and can be determined empirically from testing, by mathematical methods such as finite element analysis (FEA), and from application of vertical loads to the underside of the tool 49 whilst observing the output of the crystal 52.

Figure 10:
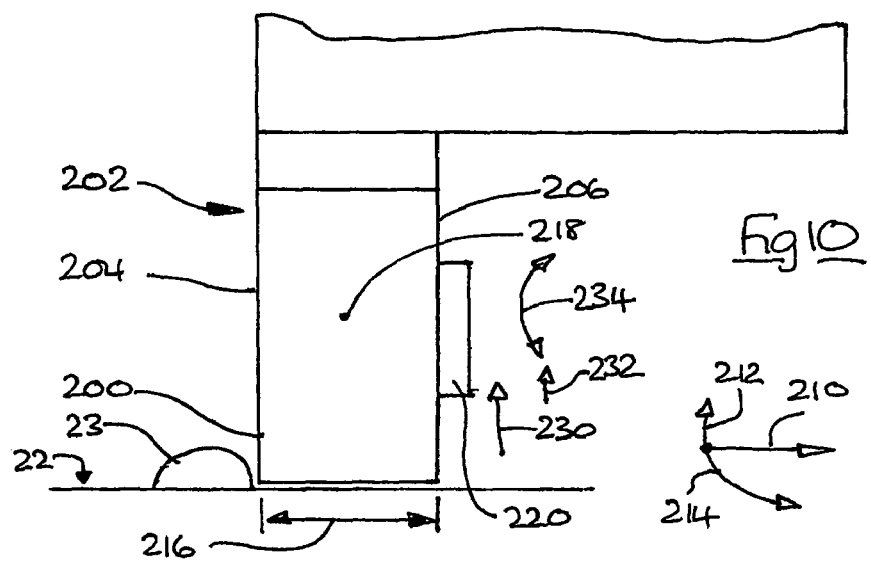
FIG. 10 depicts the forces on a shear tool not having an offset ball deposit contact surface.

To understand the benefit of the embodiment of the shear tool 49 having a contact face 54 setback from the front face 50, as compared to a shear tool such as shear tool 18 having no setback, reference is made to FIG. 10. In FIG. 10, as the front face 200 of a shear tool 202 impacts a ball deposit 23 to shear it off of substrate 22, a number of forces are produced. The ball deposit 23 pushes back against the tool 200 with a horizontal force 210. The ball deposit 23 also pushes up on the tool 202 with a vertical force 212. In addition, since the force is being applied to by ball 23 at a position which is spaced from the root of the tool 202, a bending moment 214 is applied to the tool 202. The size of the bending moment is a function of the moment arm, or distance, 216 between the contact face 200 and the root of the tool 202. The horizontal force 210 places the front face 204 of the tool in tension and the rear face 206 in compression as previously described. As a result, piezo-electric crystal 220 experiences a compressive force 230 produced by the horizontal force 210, a compressive force 232 corresponding to the vertical force 212, and a force 234 placing the crystal 220 in tension corresponding to the bending moment 214. The tension force 234 is likely to be more significant than the compressive force 232 with the result that this tension force 234 will tend to cancel a part of the force 230, resulting in an inaccurate sheer force measurement.

Figure 11:
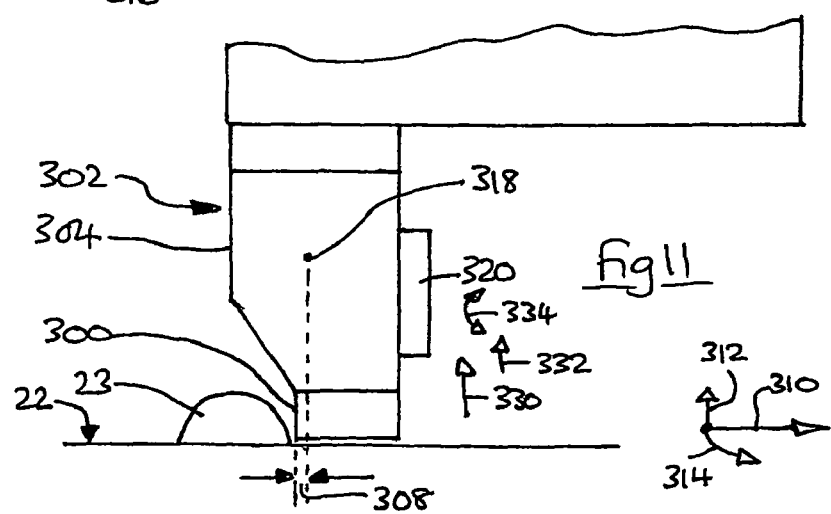
FIG. 11 depicts the forces on a shear tool having an offset ball deposit contact surface.

To minimize or reduce this inaccuracy, as shown in FIG. 11, the contact face 300 of the shear tool 302 is offset rearwardly from the front face 304. The effect of this offset is to bring the contact face 300 closer to the center of bending 318 of the tool 302. This reduces the moment arm 308, and thus the bending moment 314. The result is that the tool 302 still experiences the same horizontal force 310 which results from a ball deposit 23 pushing back against the tool 302. The tool 202 also experiences the same vertical force 312 caused by the ball deposit 23 pushing up on the tool 302. However since the moment arm 308 has been shortened, the bending moment 314 has been correspondingly reduced compared to the bending moment 214 in FIG. 10. Consequently, while the piezo-element 320 still experiences the same compressive force 330 corresponding to the horizontal force 310, and the same compressive force 332 corresponding to the vertical force 312, the tension force 334 resulting from the bending moment 314 is significantly reduced. Ideally, the geometry of the tool is designed such that the tension force 334 resulting from the bending moment 314 is roughly equivalent to the compression force 332 with the result that these forces substantially cancel each other out so that the piezo-electric crystal 320 produces an electrical signal corresponding only to the compressive force 330 which results from the horizontal force 310. In this way, the crystal 320 is producing a force that more accurately reflects just the amount of force necessary to shear the ball deposit 23 off of substrate 22.

Figure 12:
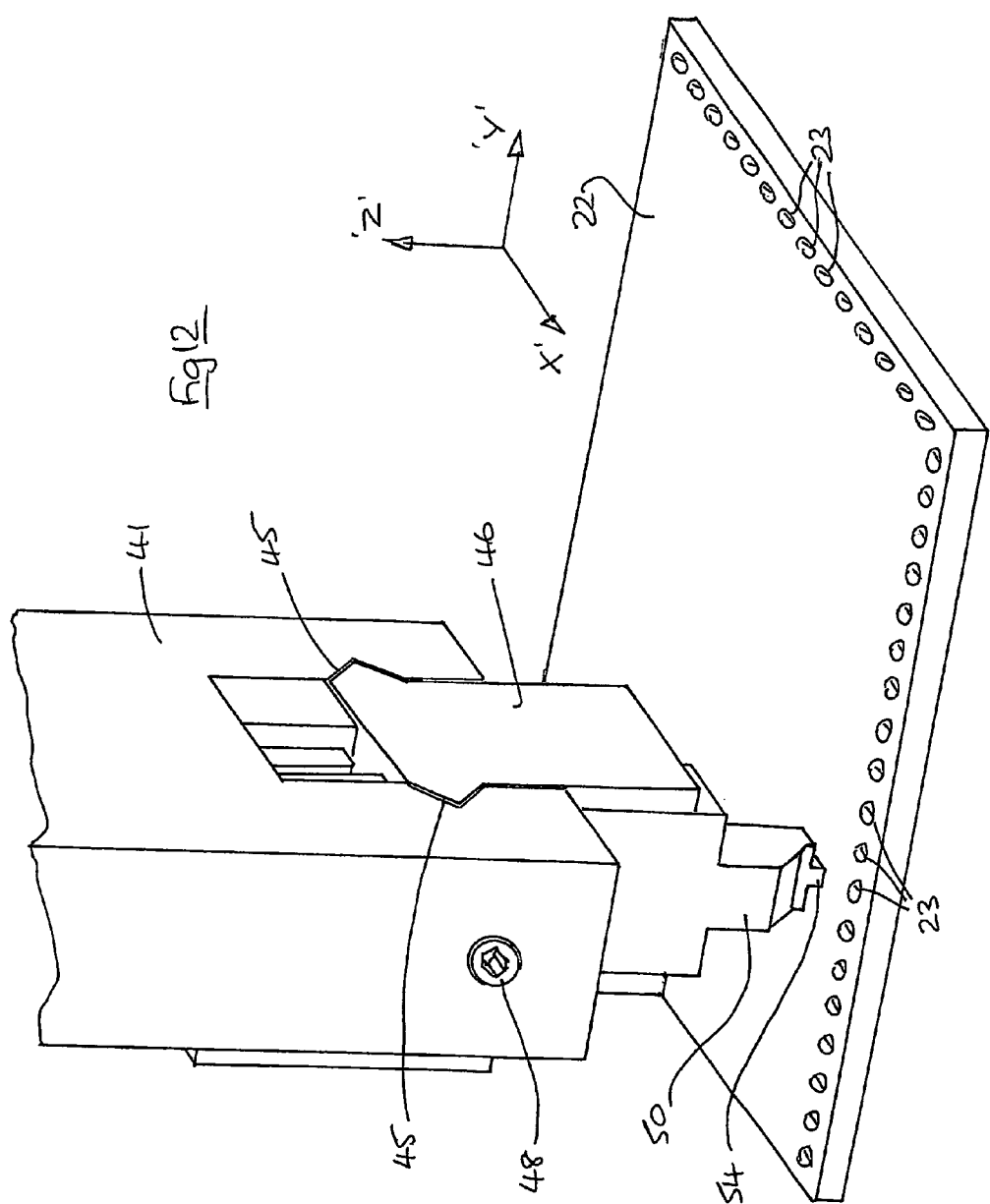
FIG. 12 is a representation of the variant tool in use.

FIG. 12 shows a three dimensional representation of a stepped-back tool 49 prior to application of a shear force to one of a row of ball deposits.

Typically the width of the contact face 52 is approximately the same as the diameter of the ball deposit, and may be about 100-750 μm. The use of a replaceable inset permits different widths of tool to be provided, and tools with different form (for example tools having a shaped recess adapted to the shape of the ball deposit).

It is intended to be understood that this invention is not limited to the embodiments described herein and that variants, obvious to those skilled in the art, can be made which are within the spirit of the invention and scope of the apparatus and method claims appended hereto. For example, while the piezo-electric crystal is shown in these embodiments only on the rear face of the shear tool in the embodiments depicted, the piezo-electric crystal could alternately be provided on the front face or other surfaces of the shear tool. Other such modifications could also be made.

The invention claimed is:

1. A test apparatus for applying shear forces to an electrically conductive deposit on a substrate to test the shear strength of the bond therebetween, the apparatus comprising a shear tool with a front face and a back face, and a piezo-electric crystal mounted on the back face of the shear tool, the front face of the shear tool being adapted to apply a shear force to said deposit, and said crystal being arranged to be placed under stress caused by forces of compression or tension acting along said shear tool while said shear tool is applying said shear force to said deposit, said crystal producing an electrical signal in response to said stress, said electric signal providing an indication of the shear force required to shear the deposit off the substrate.

2. Apparatus of claim 1, further including a tool holder to which said shear tool is secured, said tool holder being adapted to be secured to a tool mover.

3. Apparatus according to claim 1 wherein a mounting face of the crystal is planar and closely adjacent the portion of the shear tool which is subjected to maximum strain during the shearing action.

4. Apparatus according to claim 1, wherein the shear tool is adapted to be secured to a tool holder as a cantilevered beam.

5. Apparatus according to claim 1, wherein the deposit is shaped as a ball and the shape of the shear tool in a region of contact with the ball deposit is selected from the group consisting of: a flat planar contact face, a one dimensional curved contact face adapted to the approximate diameter of the ball deposit, and a two-dimensional curved contact face adapted to the approximate sphericity of the ball deposit.

6. Apparatus according to claim 1, wherein said shear tool is a substantially rectangular block and the front and back faces are parallel.

7. Apparatus according to claim 1, wherein the shear tool comprises a main body portion to which the piezo-electric crystal is mounted, and a protruding contact portion of reduced size for contact with the deposit.

8. Apparatus according to claim 1, wherein said piezo-electric crystal is mounted on the shear tool by an adhesive.

9. Apparatus according to claim 8 wherein said adhesive is epoxy resin.

10. Apparatus according to claim 9 wherein the interface between the shear tool and the piezo-electric crystal comprises a force distributing layer adapted to give substantially uniform planar contact.

11. Apparatus according to claim 10 wherein said layer is sufficient to accommodate any misalignment which may be present in the respective surfaces of the shear tool and the piezo-electric crystal.

12. Apparatus according to claim 9, wherein said layer of epoxy resin provides an electrical conductor for said piezo-electric crystal.

13. Apparatus according to claim 1, wherein said front face is provided with a contact portion for contact with the deposit, wherein said contact portion is offset rearwardly from a non-contact portion of said front face.

14. Apparatus according to claim 13 wherein said contact portion comprises a contact face set back from said non-contact portion of said front face by 30-60% of the overall width of said shear tool.

15. Apparatus according to claim 14 wherein the plane of the contact face is orthogonal to the intended direction of application of shear force.

16. Apparatus according to claim 13, wherein the offset of said contact face is determined so that forces of tension and compression which act upon the piezo-electric crystal resulting from vertical forces are reduced.

17. Apparatus according to claim 1, wherein the relationship between applied shear force and electrical signal of the piezo-electric crystal is proportional.

18. Apparatus according to claim 17 wherein the relationship between applied shear force and electrical signal of the piezo-electric crystal is linear.

19. Apparatus according to claim 2 wherein said tool holder defines a mouth within which said shear tool is retained.

20. Apparatus according to claim 19 wherein said tool holder comprises a split clamp defining said mouth, and being operable to grip said shear tool.

21. Apparatus according to claim 20 wherein said tool holder comprises a body and removable cap secured thereto by screws, said body and cap defining said split clamp and said cap being adjustable with respect to said body by operation of said screws to grip said shear tool.

22. Apparatus according to claim 2, wherein said tool holder is substantially tubular and includes a cylindrical proximal end for attachment to a chuck of said tool mover.

23. Apparatus according to claim 2 wherein said tool holder and shear tool comprise complementary male and female forms allowing connection on a single linear axis perpendicular to the shearing direction of said shear tool.

24. Apparatus according to claim 23 wherein said shear tool comprises opposite projecting slide rails for reception in corresponding slide recesses of said tool holder.

25. Apparatus according to claim 24 and including a stop to limit insertion of said shear tool in said tool holder, and further including a releasable clamp to retain said shear tool in said tool holder.

26. Apparatus according to claim 23 and further including cooperating electrical contacts adapted to couple on connection of said shear tool and tool holder.

27. Apparatus according to claim 26 wherein said electrical contacts comprises sliding brushes automatically engageable in the direction of said axis.

28. Apparatus of claim 2, wherein said apparatus further includes a movable table for supporting said substrate, and further including a microscope and manual controls for positioning said shear tool with respect to said deposit on said substrate.

29. A method of determining shear forces applied to an electrically conductive deposit on a substrate, the method comprising:

providing a shear tool having a front face for shearing said deposit, and having a piezo-electric crystal bonded thereon;

providing apparatus for detecting changes in stress in said piezo-electric crystal by monitoring the electrical output thereof;

applying said front face to the deposit to shear said deposit off said substrate; and detecting change in stress in said piezo-electric crystal as said ball deposit is sheared off said substrate.

30. A method according to claim 29 and including the step of applying said shear tool at speed against said deposit.

31. A method according to claim 30 and including the step of accelerating said shear tool to terminal velocity in the range 0.5 to 10 meters per second at the point of contact with said deposit.

* * * * *